(12) United States Patent
Shin

(10) Patent No.: US 9,295,286 B2
(45) Date of Patent: Mar. 29, 2016

(54) ELECTRONIC CIGARETTE

(76) Inventor: Jong-Soo Shin, Chungbuk (KR)

( * ) Notice: Subject to any disclaimer, the term of this patent is extended or adjusted under 35 U.S.C. 154(b) by 525 days.

(21) Appl. No.: 13/822,596

(22) PCT Filed: Sep. 16, 2011

(86) PCT No.: PCT/KR2011/006857
§ 371 (c)(1),
(2), (4) Date: Mar. 12, 2013

(87) PCT Pub. No.: WO2012/081804
PCT Pub. Date: Jun. 21, 2012

(65) Prior Publication Data
US 2013/0167854 A1    Jul. 4, 2013

(30) Foreign Application Priority Data
Dec. 13, 2010   (KR) ................. 10-2010-0126649

(51) Int. Cl.
*A24F 47/00*        (2006.01)
*A61M 15/06*        (2006.01)
(Continued)

(52) U.S. Cl.
CPC ............. *A24F 47/002* (2013.01); *A24F 47/008* (2013.01); *A61M 15/0023* (2014.02); *A61M 15/06* (2013.01); *A61L 2/10* (2013.01); *A61M 2205/053* (2013.01);
(Continued)

(58) Field of Classification Search
CPC ... A24F 47/002; A24F 47/004; A24F 47/008; A61M 15/0023; A61M 15/0025; A61M 15/0026; A61M 15/06; A61M 11/003; A61M 11/042; A61M 11/044
See application file for complete search history.

(56) References Cited

U.S. PATENT DOCUMENTS

| 4,655,229 A | * | 4/1987 | Sensabaugh, Jr. | .... A24F 47/002 131/273 |
| 4,945,929 A | * | 8/1990 | Egilmex | ................ A24F 47/002 128/200.21 |

(Continued)

FOREIGN PATENT DOCUMENTS

| KR | 2003-0002086 | 1/2003 |
| KR | 2004-0067593 | 7/2004 |
| KR | 2010-0085709 | 7/2010 |

OTHER PUBLICATIONS

International Search report issued May 17, 2012 in PCT/KR2011/006857 filed Sep. 16, 2011.

(Continued)

*Primary Examiner* — Jason L Lazorcik
(74) *Attorney, Agent, or Firm* — Workman Nyedgger

(57) ABSTRACT

An electronic cigarette includes a housing having an opening, an ascending/descending means which is positioned inside the housing in order to move a cartridge up or down, the cartridge which contains a solution therein, and is moved up or down by the ascending/descending means so that the cartridge is positioned inside the housing or protrudes from the housing through the opening, an opening/closing means which opens or closes the opening by operating in cooperation with the ascending/descending means, and an ultraviolet (UV) lamp which is positioned inside the housing, and sterilizes the cartridge by irradiating the cartridge with UV radiation. When the electronic cigarette is not being used, the cartridge can be positioned inside the housing in order to prevent the cartridge from being contaminated by impurities such as dust and the cartridge can be sterilized by UV radiation emitted from the UV lamp.

15 Claims, 12 Drawing Sheets

(51) Int. Cl.
*A61M 15/00* (2006.01)
*A61L 2/10* (2006.01)

(52) U.S. Cl.
CPC ................ *A61M 2205/3331* (2013.01); *A61M 2205/8206* (2013.01); *A61M 2205/8237* (2013.01)

(56) References Cited

U.S. PATENT DOCUMENTS

| | | | | |
|---|---|---|---|---|
| 6,158,431 A * | 12/2000 | Poole | ................ | A61M 15/0085 128/200.16 |
| 6,234,167 B1 * | 5/2001 | Cox | ................ | A61M 15/0065 128/200.14 |
| 6,568,389 B1 * | 5/2003 | Rand | ................ | A61M 15/0023 128/203.15 |
| 6,575,162 B1 * | 6/2003 | Rand | ................ | A61M 15/0023 128/200.23 |
| 6,612,302 B1 * | 9/2003 | Rand | ................ | A61M 15/0065 128/200.14 |
| 6,748,946 B1 * | 6/2004 | Rand | ................ | A61M 15/0065 128/200.23 |
| 8,997,753 B2 * | 4/2015 | Li | ................ | H01C 17/00 128/202.21 |
| 2006/0016453 A1 | 1/2006 | Kim | | |
| 2007/0045288 A1 * | 3/2007 | Nelson | ................ | A61M 11/041 219/533 |
| 2013/0042865 A1 * | 2/2013 | Monsees | ................ | A61M 15/06 128/203.27 |
| 2013/0167854 A1 * | 7/2013 | Shin | ................ | A24F 47/008 131/329 |
| 2014/0339213 A1 * | 11/2014 | Bao | ................ | A61M 11/042 219/209 |
| 2015/0201676 A1 * | 7/2015 | Shin | ................ | A24F 47/008 131/329 |
| 2015/0230522 A1 * | 8/2015 | Horn | ................ | A24F 47/008 131/329 |

OTHER PUBLICATIONS

Written Opinion issued May 17, 2012 in PCT/KR2011/006857 filed Sep. 16, 2011.

* cited by examiner

ELECTRONIC CIGARETTE

TECHNICAL FIELD

The present invention relates, in general, to an electronic cigarette and, more particularly, to an electronic cigarette which includes a housing having an opening, an ascending/descending means which is positioned inside the housing in order to move a cartridge up or down, the cartridge which contains a solution therein, and is moved up or down by the ascending/descending means so that the cartridge is positioned inside the housing or protrudes from the housing through the opening, an opening/closing means which opens or closes the opening by operating in cooperation with the ascending/descending means, and an ultraviolet (UV) lamp which is positioned inside the housing, and sterilizes the cartridge by irradiating the cartridge with UV radiation, in which, when the electronic cigarette is not being used, the cartridge can be positioned inside the housing in order to prevent the cartridge from being contaminated by impurities such as dust and the cartridge can be sterilized by UV radiation emitted from the UV lamp.

BACKGROUND ART

An electronic cigarette is a product developed as an alternative to smoking tobacco, such as a cigarette, a cigar, or pipe tobacco, and has a shape similar to that of typical smoking tobacco. When smoking the electronic cigarette, a solution contained inside the electronic cigarette is vaporized by heating, ultrasonic vibration, or the like, and is discharged outward as smoke.

Smoking tobacco contains a number of harmful components, such as tar, nitroamine, hydrocarbon and carbon monoxide, which not only damage the health of a smoker, but also cause damage to the health of other people around the smoker due to passive smoking. In addition, smoke from smoking tobacco has a peculiar smell, which causes the smoker or other people around the smoker to smell unpleasant. Accordingly, over the world, places where smoking is allowed are limited according to administrative regulations, and a variety of non-smoking promotion policies are being enforced.

However, in practice, smokers cannot easily quit smoking because they are addicted to nicotine contained in tobacco. In addition, non-smoking products or tobacco substitutes fail to satisfy the desires of smokers. Therefore, an electronic cigarette was developed, which can advantageously satisfy a desire to smoke since it generates smoke by vaporizing a solution that contains nicotine or the like. In addition, unlike typical smoking tobacco, the electronic cigarette does not discharge harmful matter such as tar and does not produce an unpleasant smell.

However, in spite of a variety of advantages of the electronic cigarette, there are some problems. For instance, a cartridge of the electronic cigarette which is held in the mouth during smoking is constantly exposed to the outside and is thus easily contaminated by impurities such as dust. In particular, when the electronic cigarette is being used, saliva from the smoker sticks to the cartridge. This causes harmful bacilli to easily propagate in the cartridge, thereby putting the health of the user of the electronic cigarette at risk, and causes unpleasant sensation. In addition, when inhaling the electronic cigarette, a liquid solution that has not been sufficiently vaporized may also be discharged and enter the mouth of the smoker, causing an unpleasant taste for the smoker, which is problematic.

Therefore, there is an increasing necessity for an electronic cigarette in which the cartridge which is held in the mouth can stay clean while the advantages of the electronic cigarette can be guaranteed.

DISCLOSURE

Technical Problem

Accordingly, the present invention has been made keeping in mind the above problems occurring in the related art.

An object of the invention is to provide an electronic cigarette in which a cartridge which is held in the mouth when the electronic cigarette is being used can enter and exit a housing, so that, when the electronic cigarette is not being used, the cartridge is positioned inside the housing, thereby preventing the cartridge from being contaminated by impurities such as dust.

In addition, an object of the invention is to provide an electronic cigarette in which, when the electronic cigarette is not being used, the cartridge is positioned inside the housing, so that the cartridge can be sterilized by irradiating it with UV radiation from a UV lamp.

Furthermore, an object of the invention is to provide an electronic cigarette which includes an ascending/descending means which moves the cartridge up and down and an opening/closing means which opens or closes an opening, i.e. a passage through which the cartridge protrudes to the outside, by operating in cooperation with the ascending/descending means, thereby providing ease of use and effectively preventing the cartridge from being contaminated.

In addition, an object of the invention is to provide an electronic cigarette which includes an upper plate which is detachably coupled with the housing and forms the upper surface of the housing and a cartridge mount which protrudes inside the housing and receives an extra cartridge, thereby relieving inconvenience of carrying the extra cartridge.

Furthermore, an object of the invention is to provide an electronic cigarette which includes a pressure sensor which is pressed and generates an electric signal when the cartridge is positioned inside the housing and a lamp driving portion which operates the UV lamp for a predetermined period following the electric signal generated by the pressure sensor, so that the cartridge can be sterilized for a predetermined period as soon as the cartridge is positioned inside the housing after the electronic cigarette has been used, thereby maximizing the effect of sterilization.

In addition, an object of the invention is to provide an electronic cigarette in which a control circuit which operates the UV lamp and the vaporizer is disposed in one circuit board, so that the size of a product can be reduced.

Furthermore, an object of the invention is to provide an electronic cigarette in which a reflecting layer is formed inside the housing in order to reflect UV radiation emitted from the UV lamp, thereby maximizing the effect of sterilizing the cartridge.

In addition, an object of the invention is to provide an electronic cigarette which includes a side plate and an upper plate which are detachably coupled with each other, such that components can be easily repaired or replaced.

Furthermore, an object of the invention is to provide an electronic cigarette in which smoke that has been introduced into the cartridge is discharged to the outside after passing through a liquid separating portion, so that the smoke discharged from the electronic cigarette contains no liquid components, thereby causing no unpleasant sensation to the user of the electronic cigarette.

In addition, an object of the invention is to provide an electronic cigarette in which the area which contacts the inflow smoke is maximized in order to effectively separate minute liquid components contained in the scattering smoke.

Technical Solution

The present invention has been made keeping in mind the above problems.

In an aspect, the present invention provides an electronic cigarette that includes a housing having an opening; an ascending/descending means for moving a cartridge up or down, all or part of the ascending/descending means being positioned inside the housing; and the cartridge which contains a solution therein, and is moved up or down by the ascending/descending means so that the cartridge is positioned inside the housing or protrudes from the housing through the opening.

According to an embodiment of the invention, the electronic cigarette further includes a vaporizer which is coupled with one end of the cartridge, is supplied with the solution contained in the cartridge, and generates smoke by vaporizing the solution.

According to another embodiment of the invention, the housing includes an operating lug movement slit which is formed in one side surface thereof and extends up and down along the side surface. The ascending/descending means includes a vaporizer receiving portion which receives therein the vaporizer which is integrally coupled with the cartridge, and is to move up and down; and an operating lug which protrudes from one side surface of the vaporizer receiving portion and is inserted into the operating lug movement slit.

According to another embodiment of the invention, the electronic cigarette further includes an opening/closing means which opens or closes the opening by operating in cooperation with the ascending/descending means; and an ultraviolet lamp which is positioned inside the housing, and sterilizes the cartridge by irradiating the cartridge with ultraviolet radiation. The cartridge can be located inside the housing and the opening can be closed in order to prevent the cartridge from being contaminated by impurities and sterilize the cartridge using the ultraviolet radiation.

According to a further embodiment of the invention, the electronic cigarette further includes a vaporizer which is coupled with one end of the cartridge, is supplied with the solution contained in the cartridge, and generates smoke by vaporizing the solution.

According to further another embodiment of the invention, the housing includes an operating lug movement slit which is formed in one side surface thereof and extends up and down along the side surface. The ascending/descending means includes a vaporizer receiving portion which receives therein the vaporizer which is integrally coupled with the cartridge, and is to move up and down; and an operating lug which protrudes from one side surface of the vaporizer receiving portion and is inserted into the operating lug movement slit.

According to another embodiment of the invention, the opening/closing means includes an ascending/descending plate which is to move up and down; a door which is rotatably connected to one end of the ascending/descending plate, and opens or closes the opening following upward or downward movement of the ascending/descending plate; and a spring which connects the ascending/descending plate to the door.

According to a further embodiment of the invention, the ascending/descending means further includes a first rack gear which is formed on one side of the vaporizer receiving portion, the opening/closing means further includes a pinion gear which meshes with the first rack gear, and the ascending/descending plate has a second rack gear which is formed on one side thereof and meshes with the pinion gear.

According to further another embodiment of the invention, the electronic cigarette further includes a driving unit which is positioned inside the housing, and operates the ultraviolet lamp and the vaporizer.

According to another embodiment of the invention, the housing further includes an upper plate which is detachably coupled with the housing, thereby forming an upper surface of the housing; and a cartridge mount which protrudes inside the housing, and receives an extra cartridge therein.

According to a further embodiment of the invention, the housing further includes a leaf spring which is positioned in the operating lug movement slit, and temporarily fixes a position of the operating lug which moves up or down along the operating lug movement slit.

According to further another embodiment of the invention, the driving unit includes a pressure sensor which is pressed to transfer an electric signal to a controller when the cartridge is positioned inside; and the controller which controls an operation of the vaporizer and an operation of the ultraviolet lamp, wherein the controller comprises a lamp driving portion which operates the ultraviolet lamp for a predetermined period following the electric signal generated by the pressure sensor and a vaporizer driving portion which operates the vaporizer.

According to another embodiment of the invention, the driving unit further includes a battery which supplies power to the electronic cigarette, and the controller further comprises a battery charging portion which is supplied with external power and charges the battery.

According to a further embodiment of the invention, the cartridge includes a solution containing portion which is formed at one side of an inner surface of the cartridge, and contains the solution therein; an inflow passage through which smoke that is generated while the solution contained in the solution containing portion is passing through the vaporizer is introduced; a liquid separating portion which removes liquid components contained in the smoke that is introduced through the inflow passage; and a discharge hole through which the smoke, the liquid components of which are removed by the liquid separating portion, is discharged to an outside. The liquid separating portion includes a lower wing plate which is positioned above the inflow passage, protrudes from one portion of an inner surface of the cartridge, and extends a predetermined length in an opposite direction, and an upper wing plate which is positioned above the lower wing plate, protrudes from the other portion opposite one portion from which the lower wing plate protrudes, and extends a predetermined length in a direction in which the lower wing plate protrudes, whereby, as the smoke that has been introduced through the inflow passage and the liquid components in the smoke comes into contact with the liquid separating portion, a vortex flow is created and a speed of the smoke is decreased, so that the liquid components form droplets on and are trapped by the liquid separating portion.

According to further another embodiment of the invention, the liquid separating portion further includes a trapping member which is connected to a distal end of the upper wing plate, the trapping member having at least one multifaceted member therein.

According to another embodiment of the invention, each of the lower wing plate and the upper wing plate has a shape of a wave, and is inclined more downward in a direction toward a distal end thereof.

According to further another embodiment of the invention, the lower wing plate further includes a porous member which is positioned at the distal end of the lower wing plate and has a plurality of cavities.

Advantageous Effects

The invention can realize the following effects from the above-described embodiments, as well as constructions, combinations and relationships of use which will be described later.

According to the invention, the cartridge which is held in the mouth when the electronic cigarette is being used can enter and exit the housing, so that, when the electronic cigarette is not being used, the cartridge is positioned inside the housing, thereby preventing the cartridge from being contaminated by impurities such as dust.

In addition, according to the invention, when the electronic cigarette is not being used, the cartridge is positioned inside the housing, so that the cartridge can be sterilized by irradiating it with UV radiation from the UV lamp.

Furthermore, according to the invention, the electronic cigarette includes the ascending/descending means which moves the cartridge up and down and the opening/closing means which opens or closes an opening, i.e. the passage through which the cartridge protrudes to the outside, by operating in cooperation with the ascending/descending means, thereby providing ease of use and effectively preventing the cartridge from being contaminated.

In addition, according to the invention, the upper plate is detachably coupled with the housing and forms the upper surface of the housing, and the cartridge mount protrudes inside the housing and receives an extra cartridge, thereby relieving inconvenience of carrying the extra cartridge.

Furthermore, according to the invention, the pressure sensor is pressed and generates an electric signal when the cartridge is positioned inside the housing and the lamp driving portion which operates the UV lamp for a predetermined period following the electric signal generated by the pressure sensor, so that the cartridge can be sterilized for a predetermined period as soon as the cartridge is positioned inside the housing after the electronic cigarette has been used, thereby maximizing the effect of sterilization.

In addition, according to the invention, the control circuit which operates the UV lamp and the vaporizer is disposed in one circuit board, so that the size of a product can be reduced.

Furthermore, according to the invention, the reflecting layer is formed inside the housing in order to reflect UV radiation emitted from the UV lamp, thereby maximizing the effect of sterilizing the cartridge.

In addition, according to the invention, the electronic cigarette includes the side plate and the upper plate which are detachably coupled with each other, such that components can be easily repaired or replaced.

Furthermore, according to the invention, smoke that has been introduced into the cartridge is discharged to the outside after passing through the liquid separating portion, so that the smoke discharged from the electronic cigarette contains no liquid components, thereby causing no unpleasant sensation to the user of the electronic cigarette.

In addition, according to the invention, the area which contacts the inflow smoke is maximized in order to effectively separate minute liquid components contained in the scattering smoke.

Figure 1:
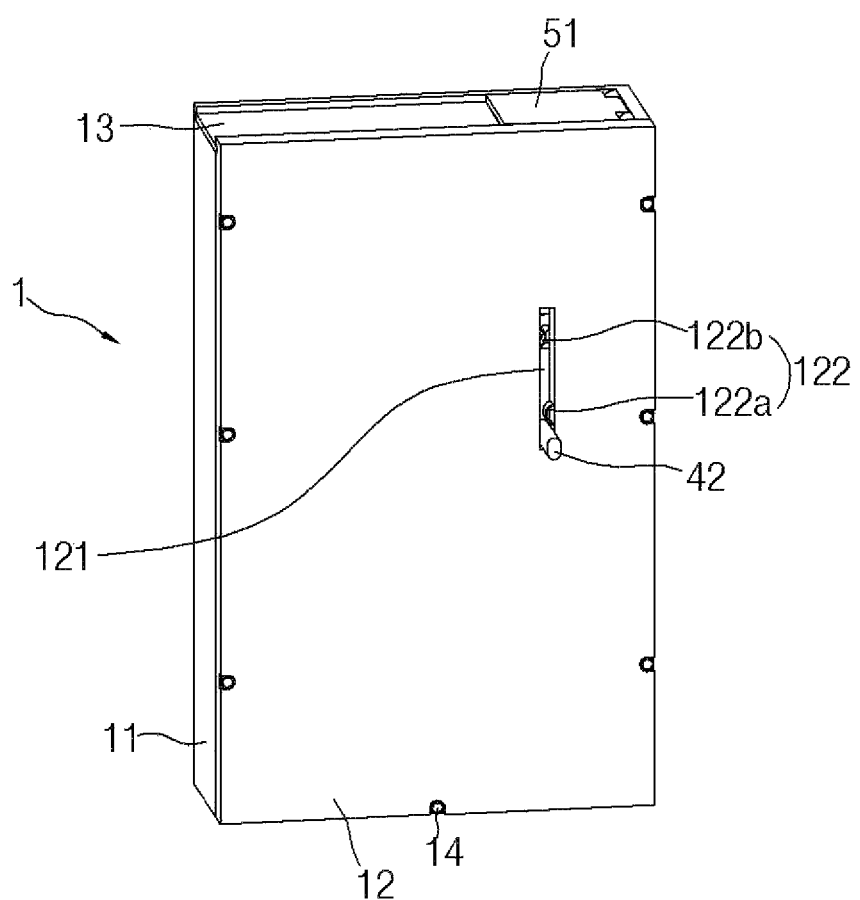
FIG. 1 a front perspective view of an electronic cigarette according to an embodiment of the invention.

| *Major Reference Numerals and Symbols of the Drawings* | |
|---|---|
| 1: housing | 11: channel |
| 12: side plate | 13: upper plate |
| 14: coupling means | 15: upper plate guide groove |
| 16: ascending/descending plate guide | |
| 111: receiving portion guide | |
| 112: cartridge mount | 113: lamp socket |
| 114: door support protrusion | |
| 115: gear coupling protrusion | |
| 121: operating lug movement slit | |
| 122: leaf spring | 111a: sensor receiving recess |
| 2: vaporizer | 21: air inlet hole |
| 22: vaporizing portion | |
| 221: solution collecting portion | |
| 222: heating coil | 3, 3'': cartridge |
| 31: pressed portion | |
| 32: solution containing portion | |
| 33: fiber member | 34: inflow passage |
| 35: discharge hole | |
| 36: liquid separating portion | |
| 321: entrance recess | 361: lower wing plate |
| 362: upper wing plate | 363: trapping member |
| 3611: porous member | 3631: multifaceted member |
| 4: ascending/descending means | |
| 41: vaporizer receiving portion | |
| 42: operating lug | 43: first rack gear |
| 411: vaporizer receiving recess | |
| 412: through-hole | 5: opening/closing means |
| 51: door | 52: ascending/descending plate |
| 53: pin | 54: spring |
| 55: pinion gear | 55a: through-hole |
| 521: second rack gear | 6: UV lamp |
| 7: driving unit | 71: pressure sensor |
| 72: battery | 73: power supply |
| 74: input | 75: controller |
| 731: power connector | 741: operating button |
| 751: vaporizer driving portion | |
| 752: lamp driving portion | |
| 753: battery charging portion | |
| 754: controlling portion | |

BEST MODE

Reference will now be made in detail to an electronic cigarette according to the present invention, embodiments of which are illustrated in the accompanying drawings and described below. Throughout this document, reference should be made to the drawings, in which the same reference numerals and signs are used throughout the different drawings to designate the same or similar components. In the following description of the present invention, detailed descriptions of known functions and components incorporated herein will be omitted when they may make the subject matter of the present invention unclear. Unless specifically defined, all terms used in the specification are interpreted as common meanings of the terminologies that a person having ordinary skill in the art to which the invention pertains understands. When a term is not compliant with the common meaning, the term should be interpreted based on the definition in the specification.

Figure 2:
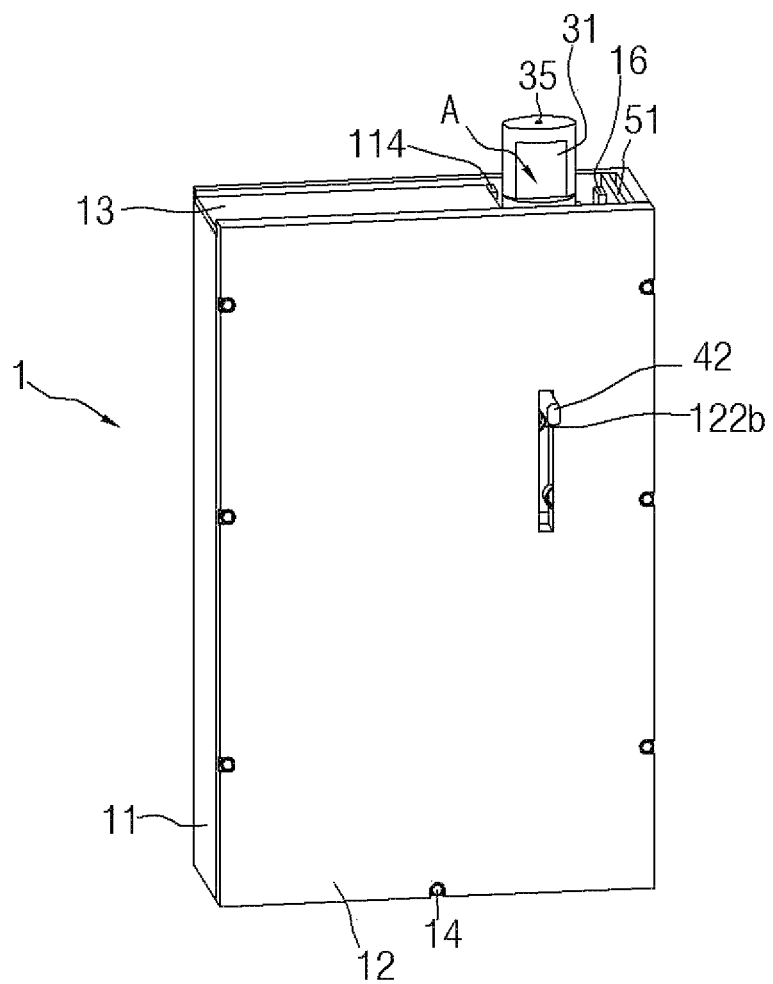
FIG. 2 is a front perspective view of the electronic cigarette according to an embodiment of the invention in which the cartridge is protruded outward.
Figure 3:
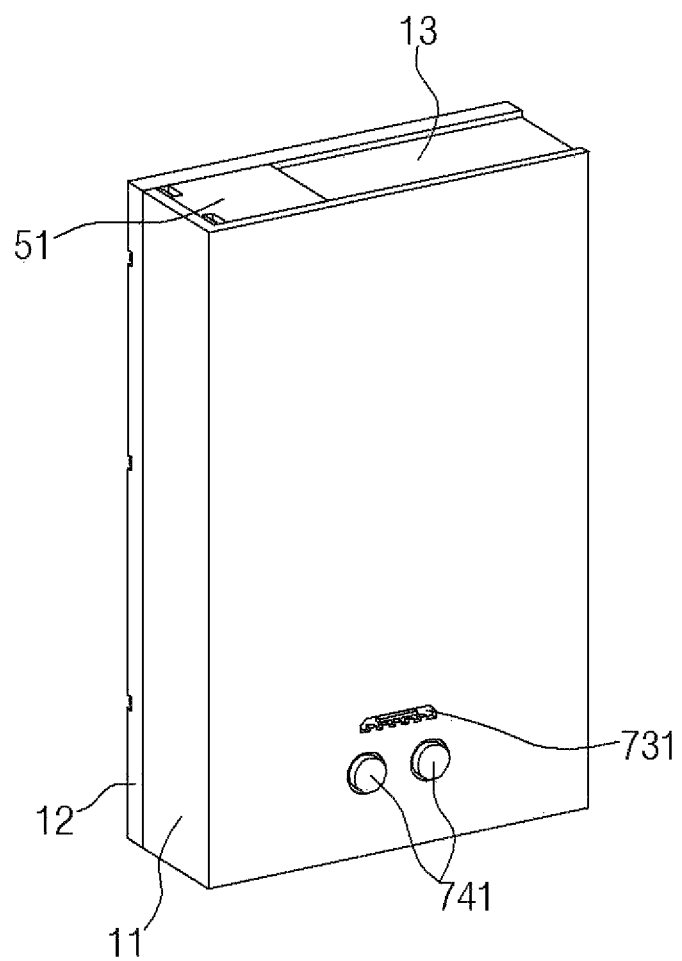
FIG. 3 is a rear perspective view of the electronic cigarette according to an embodiment of the invention.
Figure 4:
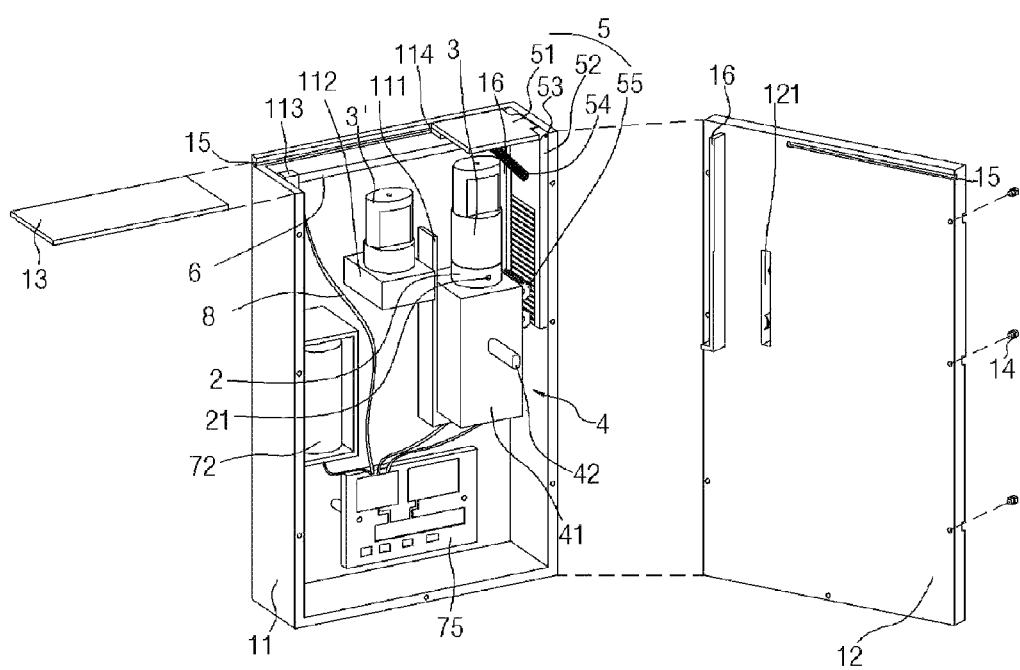
FIG. 4 is an exploded perspective view of the electronic cigarette according to an embodiment of the invention.
Figure 5:
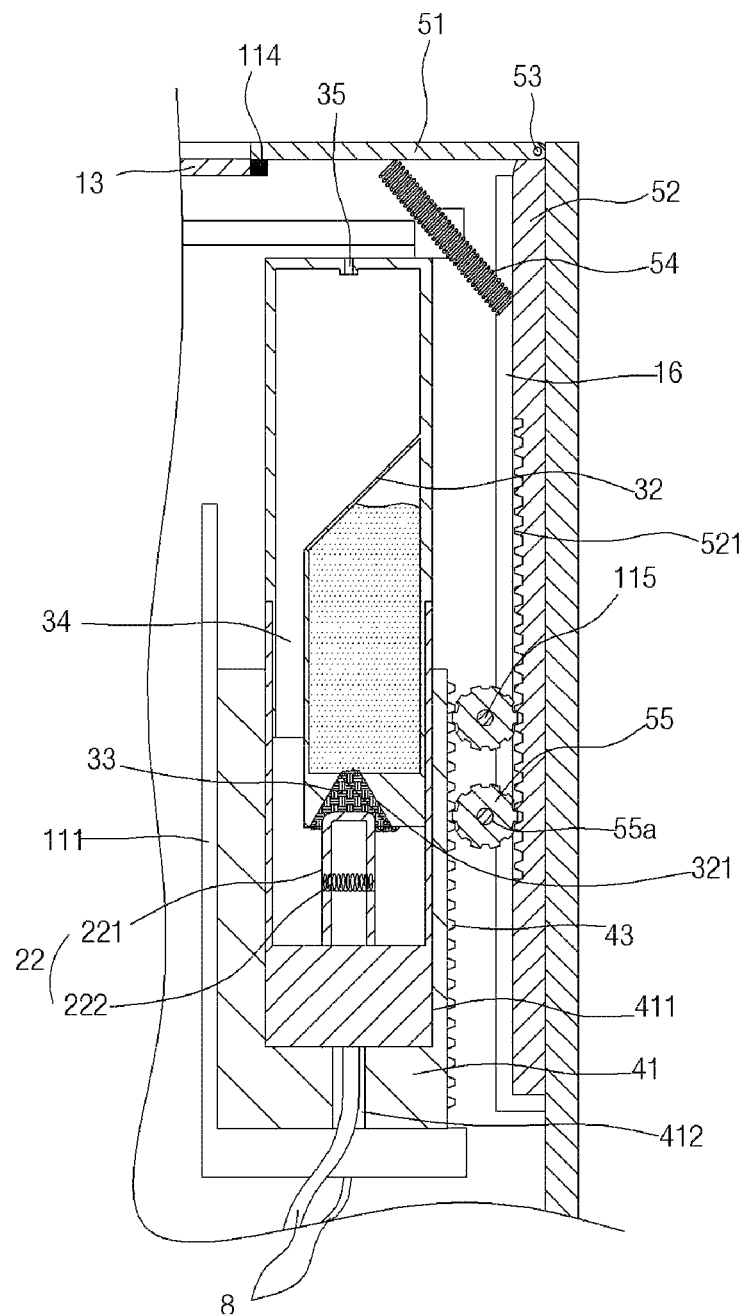
FIG. 5 is a cross-sectional view of key parts of the electronic cigarette according to an embodiment of the invention.
Figure 6:
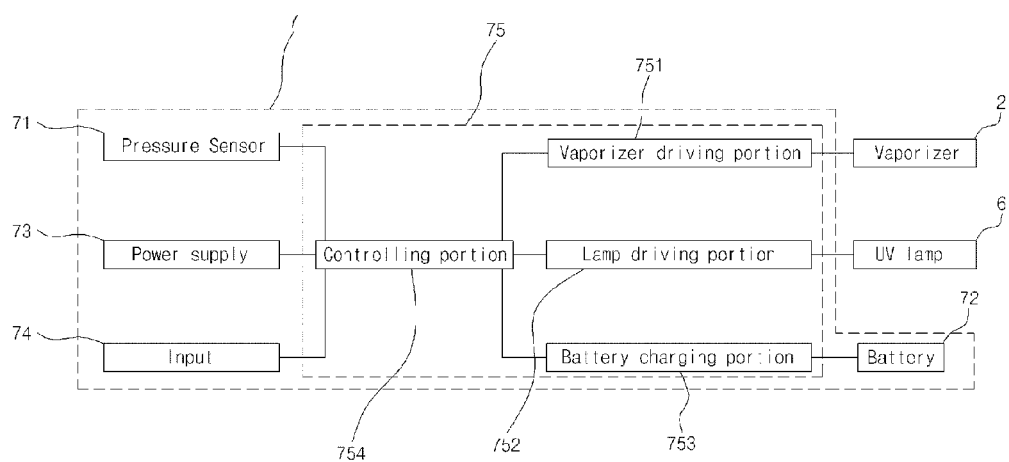
FIG. 6 is a block diagram of the driving unit included in the electronic cigarette according to an embodiment of the invention.
Figure 7:
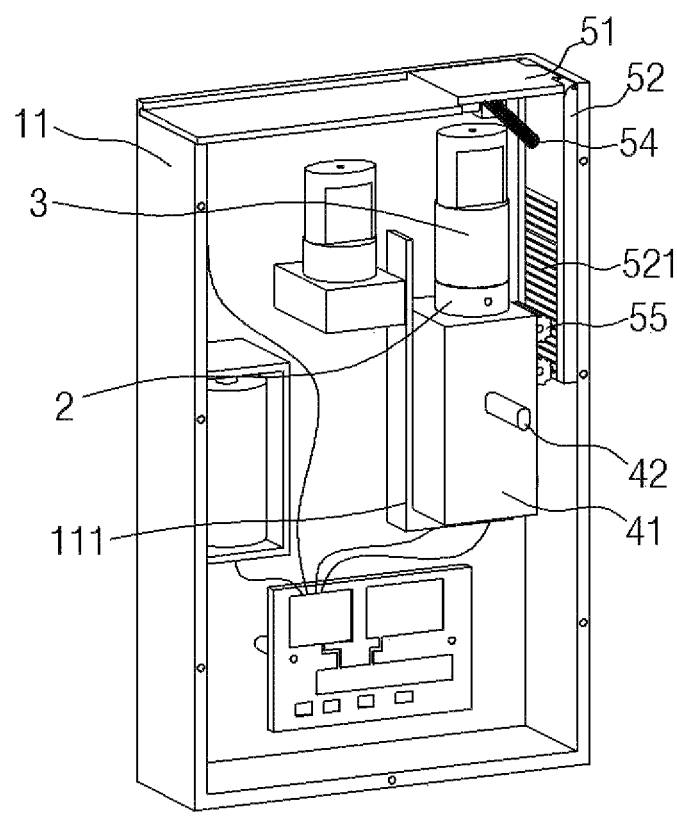
FIGS. 7 to 9 are reference views showing the operating state of the electronic cigarette according to an embodiment of the invention.
Figure 8:
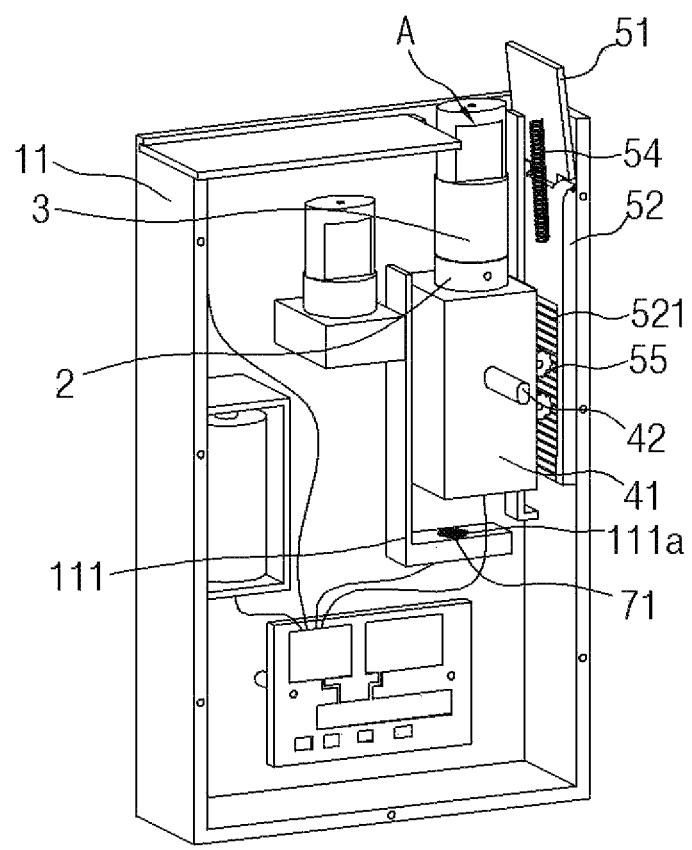
Figure 9:
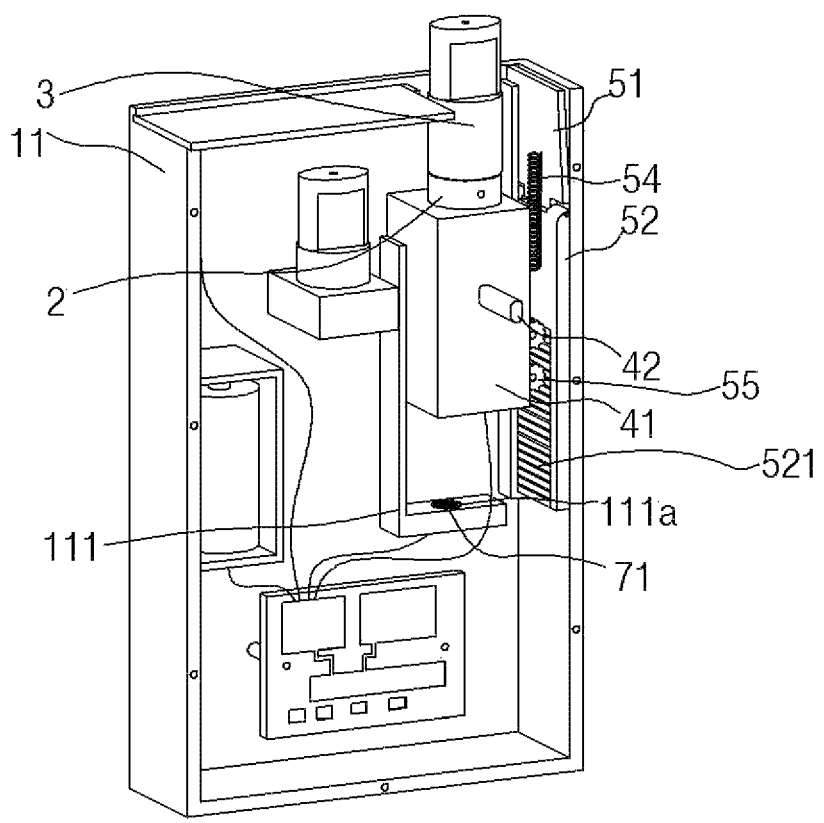
Figure 10:
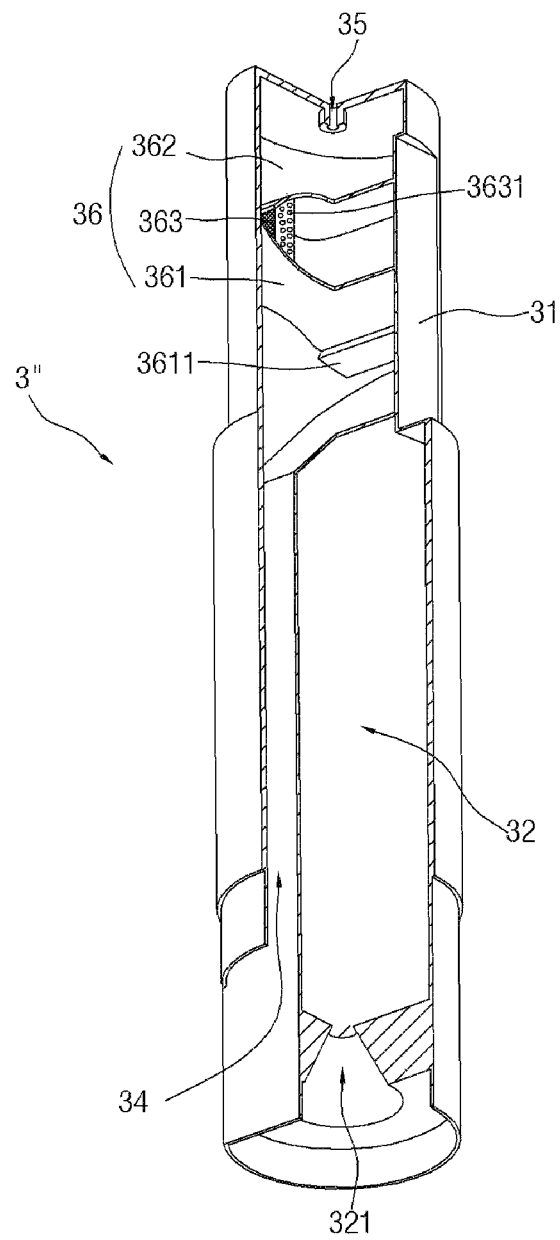
FIG. 10 is a partially-broken perspective view of the cartridge used in the electronic cigarette according to an embodiment of the invention.
Figure 11:
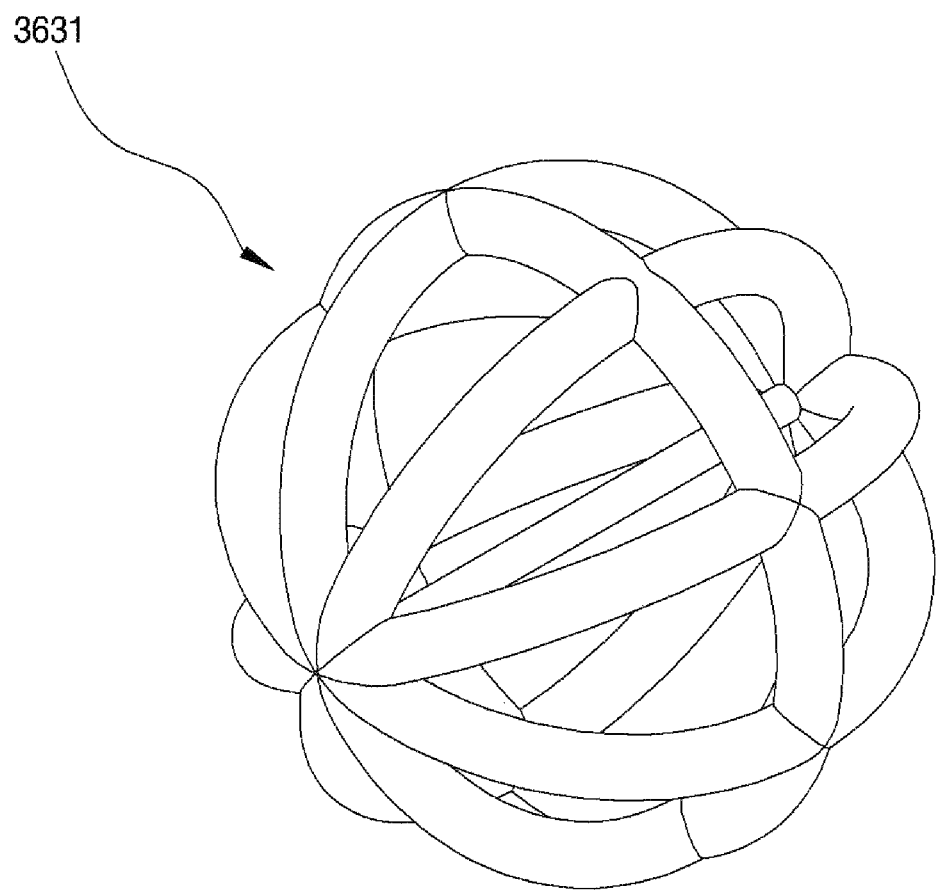
FIG. 11 is a perspective view of a multiple surface member used in an electronic cigarette according to another embodiment of the invention.
Figure 12:
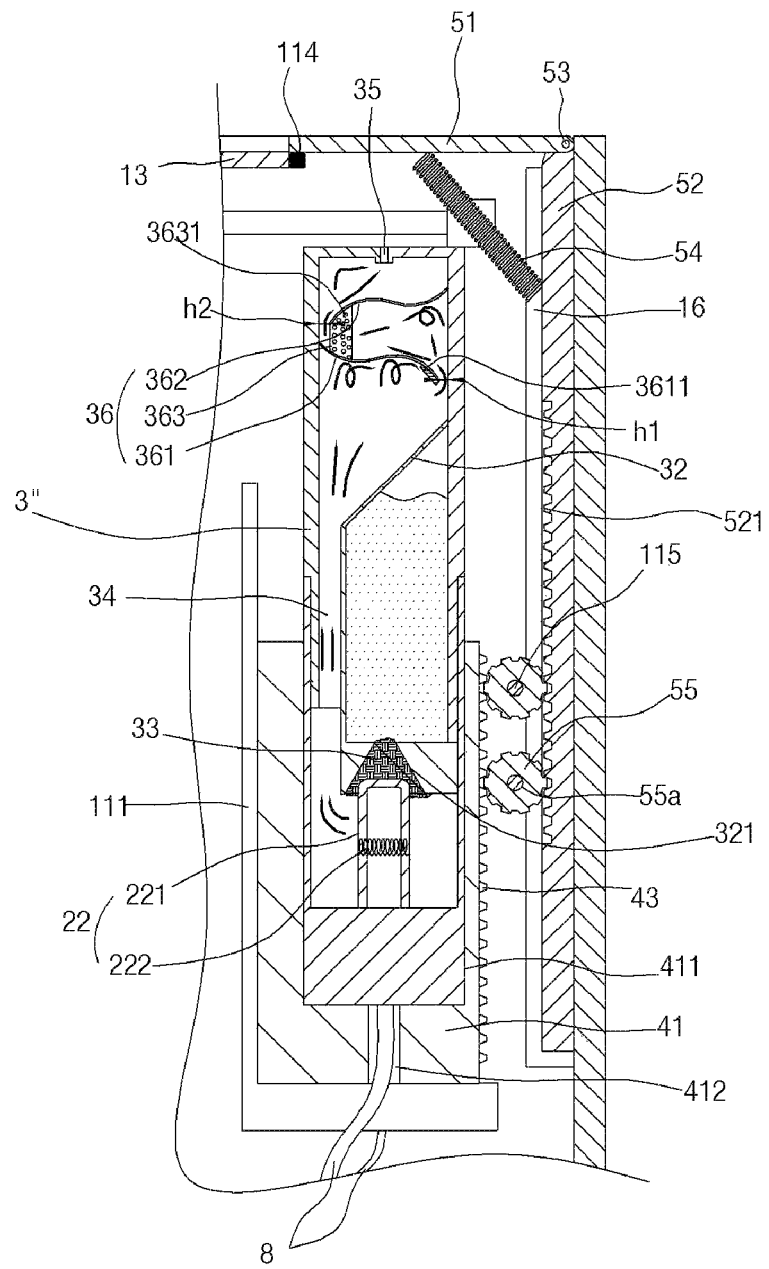
FIG. 12 is a cross-sectional view showing key parts of the electronic cigarette according to another embodiment of the invention.

FIG. 1 a front perspective view of an electronic cigarette according to an embodiment of the invention, FIG. 2 is a front perspective view of the electronic cigarette according to an embodiment of the invention in which the cartridge is protruded outward, FIG. 3 is a rear perspective view of the electronic cigarette according to an embodiment of the invention, FIG. 4 is an exploded perspective view of the electronic cigarette according to an embodiment of the invention, FIG. 5 is a cross-sectional view of key parts of the electronic cigarette according to an embodiment of the invention, FIG. 6 is a block diagram of the driving unit included in the electronic cigarette according to an embodiment of the invention, FIG. 7 to FIG. 9 are reference views showing the operating state of the electronic cigarette according to an embodiment of the invention, FIG. 10 is a partially-broken perspective view of the cartridge used in the electronic cigarette according to an embodiment of the invention, FIG. 11 is a perspective view of a multiple surface member used in an electronic cigarette according to another embodiment of the invention, and FIG. 12 is a cross-sectional view showing key parts of the electronic cigarette according to another embodiment of the invention.

An electronic cigarette according to an embodiment of the invention will be describing with reference to FIG. 1 to FIG. 9. The electronic cigarette includes a housing 1 which forms an outer shell and has an opening A, a vaporizer 2 which is positioned inside the housing 1, is supplied with a solution contained in a cartridge 3, and generates smoke by vaporizing the supplied solution, the cartridge 3 which is coupled with one end of the vaporizer 2, contains the solution therein, and discharges the smoke generated by the vaporizer 2 to the outside, an ascending/descending means 4 which is positioned inside the housing 1 and moves up and down the vaporizer 2 and the cartridge 3 which are integrally coupled with each other, an opening/closing means 5 which opens and closes the opening A by operating in cooperation with the ascending/descending means 4, an ultraviolet (UV) lamp 6 which is positioned inside the housing 1 and sterilizes the cartridge 3 by irradiating the cartridge 3 with UV radiation, and a driving unit 7 which is positioned inside the housing 1 and drives the vaporizer 2 and the UV lamp 6. When the electronic cigarette is not being used, it is possible to locate the cartridge 3 inside the housing 1 and close the opening A, thereby preventing the cartridge 3 from being contaminated with impurities, and sterilizing the cartridge 3 with UV radiation.

The housing 1 is a component which forms the outer shell of the electronic cigarette, and includes a channel 11, a side plate 12, an upper plate 13, a coupling means 14, upper plate guide grooves 15, ascending/descending plate guides 16, and the like.

The channel 11 is a component which forms part of the outer shape of the electronic cigarette, and is detachably coupled with the side plate 12 via the coupling means 14, which will be described later. The channel 11 has a predetermined shape, and preferably, the shape of a rectangular box with open front and upper portions. The channel 11 includes components such as a receiving portion guide 111, a cartridge mount 112, a lamp socket 113 and a door support protrusion 114. A reflecting layer (not shown) is formed on the upper portion of the inner surface of the channel 11 in order to reflect light that is emitted from the UV lamp 6, which will be described later, thereby increasing the efficiency of sterilizing the cartridge 3 which is positioned inside the housing 1. The reflecting layer can be formed by a variety of techniques, which includes attaching a high reflective thin metal plate to, applying a reflective paint or attaching a reflective tape on the inner surface.

The receiving portion guide 111 is a component which protrudes from the inner surface of the channel 11 and guides the up-down movement of a vaporizer receiving portion 41 of the ascending/descending means 4, which will be described later. The receiving portion guide 11 has a predetermined shape, and preferably, has an L-shaped cross-section. A sensor receiving recess 11a which receives therein a pressure sensor 71, which will be described later, is formed in the lower surface of the inner portion of the receiving portion guide 111. A hole (not shown) is formed in the lower surface of the sensor receiving recess 111a as a passage through which an electric wire 8 which connects the pressure sensor 71 to a controller 75 passes.

The cartridge mount 112 is a component which protrudes from the inner surface, and in which an extra cartridge 3' which is not being used is stored. The cartridge mount 112 has a predetermined shape, for example, the shape of a rectangular box which has a recess into which the cartridge 3 can be inserted.

The lamp socket 113 is fixed to the upper portion of the inner surface of the channel 11, is connected to the controller 75 by an electric wire 8, and supplies power to the VU lamp 6 which is fitted into the lamp socket 113. Although the lamp socket 113 can be implemented as a variety of types of sockets, a type of socket which can receive a pin-type UV lamp therein is preferably used.

The door support protrusion 114 is a component which protrudes from the upper portion of the inner surface of the channel 11 and restrains downward movement of a door 51 which closes the opening A.

A gear coupling protrusion 115 is a component which protrudes from the inner surface of the channel 11, is inserted into a through-hole 55a of a pinion gear 55, and supports the pinion gear 55.

The side plate 12 is a component which forms a side of the electronic cigarette and is detachably coupled with the channel 11 via the coupling means 14. The side plate 12 has a predetermined shape, preferably, the shape of a square plate. The side plate 12 includes components such as an operating lug movement slit 121 and leaf springs 122. A reflecting layer is formed on the upper portion of the inner surface of the side plate 12 in order to reflect UV radiation emitted from the UV lamp 6, thereby increasing the effect of sterilizing the cartridge 3.

The operating lug movement slit 121 is a component which extends up and down along the side plate 12 so as to receive an operating lug 42, which will be described later. The operating lug movement slit 121 guides the operating lug 42 so that the operating lug 42 can be inserted into and be moved up and down along the slit 121.

The leaf springs 122 are disposed at one side of the side plate 12, and protrude from the operating lug movement slit 121, such that they temporarily fix the position of the operating lug 42 which moves up and down along the operating lug movement slit 121. The leaf springs 122 are respectively located in the upper and lower portions of the operating lug movement slit 121, and cause the operating lug 42 to be temporarily fixed at the uppermost and lowermost portions of the operating lug movement slit 121. When a user moves the operating lug 42, the operating lug 42 presses and pushes the leaf springs 122 so that it can freely move. When the operating lug 42 is not moved any further, the leaf springs 122 contract and protrude in the operating lug movement slit 121, thereby fixing the operating lug 42.

The upper plate 13 is a component which forms part of the upper surface of the electronic cigarette, and is detachably coupled with the channel 11 and the side plate 12. The upper plate 13 has a predetermined shape, preferably, the shape of a rectangular plate. Since the upper plate 13 forms part of the upper surface of the electronic cigarette, the portion that is not covered by the upper plate 13 will hereinafter be referred to as an opening A. A reflecting layer is formed on the lower surface of the upper plate 13 in order to reflect UV radiation emitted from the UV lamp 6, thereby increasing the effect of sterilizing the cartridge 3.

The coupling means 14 is a component which detachably couples the channel 11 and the side plate 12 with each other. The coupling means 14 can be implemented as various means which can detachably couple the channel 11 and the side plate 12 with each other, for example, a screw.

The upper plate guide grooves 15 are horizontal grooves that are cut into the inner surfaces of the channel 11 and the side plate 11. As the upper plate 13 is inserted into the upper plate guide grooves 15, the upper plate 13 can be detachably coupled with the channel 11 and the side plate 12.

The ascending/descending plate guides 16 are components which respectively protrude from the inner surfaces of the channel 11 and the side plate 12 such that they guide the upward and downward movement of an ascending/descending plate 52 of the opening/closing means 5, which will be described later. The ascending/descending plate guides 16 have a predetermined shape, and preferably, have an L-shaped cross-section. The ascending/descending plate guides 16 which respectively protrude from the channel 11 and the side plate 12 face each other at a predetermined distance. The above-described electronic cigarette can maximize the effect of sterilizing the cartridge 3 since the reflecting layers formed inside the housing 1 reflect UV radiation emitted from the UV lamp 6. In addition, the electronic cigarette is characterized by the upper plate 13 which is detachably coupled with the housing 1 to form the upper surface of the housing 1 and the cartridge mount 112 which protrudes inside the housing 1 so as to receive the extra cartridge 3' therein. Since it is possible to store the cartridge 3', which is new or used, in addition to the cartridge 3 coupled with the vaporizer 2, by opening the upper surface of the housing 1, the inconvenience of storing the extra cartridge 3' separately from the electronic cigarette can be removed. In addition, the electronic cigarette is characterized by the side plate 12 and the upper plate 13 which are detachably coupled with each other, such that components can be easily repaired and replaced.

One end of the vaporizer 2 is positioned inside the housing 1 and the other end of the vaporizer 2 is coupled with the cartridge, such that the vaporizer 2 receives a solution contained in the cartridge 3 and generates smoke by vaporizing the solution. The vaporizer 2 is disposed as being inserted into the vaporizer receiving portion 41 of the ascending/descending means 4, and is connected to the controller 75 via an electric wire 8. The vaporizer 2 includes components such as an air inlet hole 21 and a vaporizing portion 22.

The air inlet hole 21 is a through-hole formed in one surface. When a user of the electronic cigarette breathes in, external air flows inward through the air inlet hole 21.

The vaporizing portion 22 is a component which is positioned inside the vaporizer 2, receives the solution contained in the cartridge 3, and generates smoke. The vaporizing portion 22 includes components such as a solution collecting portion 221 and a heating coil 222. The solution collecting portion 221 is configured such that the distal end thereof is in contact with a fiber member 33 of the cartridge 3 in order to absorb the solution, and can be made of, for example, polyester foam or stainless fiber foam. One portion of the heating coil 222 is connected to the solution collecting portion 221, and the heating coil 222 generates smoke by heating the solution that has permeated into a vessel through the solution collecting portion 221 and converting the solution into the gaseous state.

The cartridge 3 is a component which is coupled with one end of the vaporizer 2, contains the solution therein, and discharges the smoke generated by the vaporizer 2 to the outside. The upper end of the outer surface of the cartridge 3 is inserted into the lower end of the inner surface of the vaporizer 2 such that the vaporizer 2 is coupled with the cartridge 3. The distal end of the solution collecting portion 221 of the vaporizer 2 is in contact with the fiber member 33 of the cartridge 3. The cartridge 3 has components, including a pressed portion 31 in the upper end thereof which is vertically compressed such that a smoker can easily bite the electronic cigarette, a solution containing portion 32 which is formed at one portion of the inner surface so as to contain the solution therein, the fiber member 33 which is inserted into an entrance recess 321 of the solution containing portion 32 so as to absorb the solution contained in the solution containing portion 32, an inflow passage 34 through which the smoke that is generated while the solution contained in the solution containing portion 32 is passing through the vaporizer 2 is introduced, and a discharge hole 35 through which the smoke introduced through the inflow passage is discharged to the outside.

Referring to FIG. 10 to FIG. 12, a description will be given of a cartridge used in an electronic cigarette according to another embodiment of the invention. The cartridge 3" is the same as the cartridge 3 which has been described with reference to FIG. 1 to FIG. 9, except that a liquid separating portion 36 is additionally included. Therefore, only the liquid separating portion 36 will be described below.

The liquid separating portion 36 is a component which is positioned above the inflow passage 34, and removes liquid components included in the smoke that is introduced through the inflow passage 34. The liquid separating portion 36 includes a lower wing plate 361, an upper wing plate 362, a trapping member 363, and the like.

The lower wing plate 361 is a plate which is positioned above the inflow passage 34, protrudes from the inner surface of the cartridge surrounding the inflow passage 34, extends a predetermined length in the opposite direction, and is inclined more downward in the direction toward the distal end. The smoke introduced through the inflow passage 34 comes into contact with the lower wing plate 361. It is preferred that the lower wing plate 361 have a wave-like shape in order to maximize the area in which it contacts the inflow smoke and to guide the smoke so as to smoothly flow. The smoke is directed in the direction toward a first gap h1 that is formed between the inner surface of the cartridge and the lower wing plate 361, and comes into contact with the lower wing plate 361 several times, thereby increasing the contact area, and decreases in pressure and speed, thereby increasing the time for which the smoke contacts the lower wing plate 361. At this time, some of the liquid components contained in the smoke form droplets on the lower wing plate 361, which in turn fall due to gravity. The lower wing plate 361 can include a porous member 3611 at the distal end thereof which includes a plurality of cavities.

The porous member 3611 is positioned at the distal end of the lower wing plate 361, and has a number of cavities which communicate with each other in the shape of a net such that the liquid components can permeate between the cavities. This increases the ratio of absorption of the liquid components. With this configuration, the liquid components contained in the smoke that is passing through the porous member 3611 and the liquid components that formed droplets on the lower wing plate 361 flow along the lower wing plate 361, and are then absorbed in the porous member 3611. The liquid components absorbed in the porous member 3611 gradually condense and form liquid droplets, which increase in weight and fall freely. The porous member 3611 can be implemented as any material that has a plurality of cavities. As an exemplary embodiment of the porous member 3611, sponge or the like, which can absorb liquid components, can be used.

The upper wing plate 362 is positioned above the lower wing plate 361, protrudes from the other side that is opposite a side from which the lower wing plate 361 protrudes, extends a predetermined length in the direction in which the lower wing plate 361 protrudes, and is inclined more downward in the direction toward the distal end. The smoke that has entered through the first gap h1 comes into contact with the upper wing plate 362. It is preferred that the upper wing plate 362 have a wave-like shape in order to maximize the area in which it contacts the inflow smoke and to guide the smoke so as to smoothly flow. The smoke is directed in the direction toward a second gap h2 that is formed between the inner surface of the cartridge and the upper wing plate 362, and comes into contact with the upper wing plate 362 several times, thereby increasing the contact area, and decreases in pressure and speed, thereby increasing the time for which the smoke contacts the upper wing plate 362. At this time, some of the liquid components contained in the smoke form droplets on the upper wing plate 362, which in turn fall due to gravity.

The trapping member 363 is a part which is positioned at the distal end of the upper wing plate 362 and finally separates the liquid components contained in the smoke. The trapping member 363 extends from the distal end of the upper wing plate 362 to the undersurface of the lower wing plate 361. It is preferred that the trapping member 363 have the shape of a net through which the smoke can pass. At least one multifaceted member 3631 can be included inside the trapping member 363 in order to increase the area which contacts the smoke that passes through the trapping member 363.

The multifaceted member 3631 is a member which is included in the trapping member 363 in order to increase the area which contacts the smoke that passes through the multifaceted member 3631. It is preferred that the multifaceted member 3631 has a three-dimensional shape made of a net in order to maximize the area which contacts the smoke that passes through the multifaceted member 3631. Referring to FIG. 11, the multifaceted member 3631 can be configured as a three-dimensional member having the shape of a globe in which the outer surface and the inside are made of a net and the inside is not filled. In this case, the smoke that passes through the multifaceted member 3631 passes through the net in the outer surface, the inside, and then the net in the outer surface of the multifaceted member 3631, thereby increasing the contact area and decreasing the pressure and speed. Consequently, some of the liquid components contained in the smoke form droplets on the multifaceted member 3631 or the trapping member 363, which in turn freely fall due to gravity.

The liquid separating portion 36 having the above-described configuration can separate the liquid components contained in the smoke using not only the upper wing plate 362 and the lower wing plate 361, but also the porous member 3611 and the multifaceted member 3631, thereby maximizing the efficiency of removing the liquid components from the smoke. In addition, the liquid separated by the liquid separating portion 36 flows down in the direction toward the liquid collecting portion 221, so that the separated liquid components can be reused.

The ascending/descending means 4 is a component which is positioned inside the housing 1, and moves up and down the vaporizer 2 and the cartridge 3 which are integrally coupled with each other. The ascending/descending means 4 includes components such as the vaporizer receiving portion 41, the operating lug 42 and a first rack gear 43.

The vaporizer receiving portion 41 is a component which receives the vaporizer 2 therein, and moves up and down inside the housing 1, guided by the receiving portion guide 111. The vaporizer receiving portion 41 has a predetermined shape, preferably, the shape of a rectangular box including a vaporizer receiving recess 411 which is concaved downward. A through-hole 412 is formed in the lower surface of the vaporizer receiving recess 411. The through-hole 412 acts as a passage through which the electric wire which connects the vaporizer 2 to the controller 75 passes.

The operating lug 42 is a component which extends from the front surface of the vaporizer receiving portion 41, is inserted into the operating lug movement slit 121, and protrudes from the front surface of the side plate 12. The operating lug 42 is movable up and down in the operating lug movement slit 121.

The first rack gear 43 is a component which protrudes from one side of the vaporizer receiving portion 41 and meshes with the pinion gear 55 of the opening/closing means 5, which will be described later. The first rack gear 43 rotates the pinion gear 55 following the upward and downward movement of the vaporizer receiving portion 41. When the user of the electronic cigarette moves the operating protrusion 42 up, the cartridge 3 protrudes from the housing 1. The related operating principle will be described in detail later.

The opening/closing means 5 is a component which operates in cooperation with the ascending/descending means 4 and opens/closes the opening A. The opening/closing means 5 includes components such as the door 51, the ascending/descending plate 52, a pin 53, a spring 54 and the pinion gear 55.

The door 51 is a component which is rotatably connected to one end of the ascending/descending plate 52, which will be described later, and opens/closes the opening A following upward and downward movement of the ascending/descending plate 52. The door 51 has a predetermined shape, for example, the shape of a rectangular plate. The door 51 can be rotatably coupled with the ascending/descending plate 52 via the pin 53. A reflecting layer is formed on the undersurface of the door 51 in order to reflect UV radiation emitted from the UV lamp 6, thereby increasing the efficiency of sterilizing the cartridge 3.

The ascending/descending plate 52 is a component which is rotatably connected to the door 51, and opens/closes the door 51 through upward and downward movement. The ascending/descending plate 52 moves up and down in cooperation with the ascending/descending means 4, guided by the ascending/descending plate guide 16. A second rack gear 521 which meshes with the pinion gear 55 is formed on one side of the ascending/descending plate 52. The ascending/descending plate 52 moves up and down following rotation of the pinion gear 55.

One end of the spring 54 is connected to the inner surface of the door 51 and the other end of the spring 54 is connected to the upper portion of the inner surface of the ascending/descending plate 52 so as to provide an elastic force.

In the state in which the gear coupling protrusion 115 is inserted into the through-hole 55*a*, the pinion gear 55 is positioned between the vaporizer receiving portion 41 and the ascending/descending plate 52, and meshes with the first rack gear 43 and with the second rack gear 521. The pinion gear 55 rotates following upward and downward movement of the first rack gear 43, thereby moving the second rack gear 521 up and down. The opening/closing means 5 opens the opening A in cooperation with the ascending/descending means 4. The related operating principle will be described in detail later.

The UV lamp 6 is a component which is inserted into the lamp socket 113, and emits UV radiation under the control of the driving unit 7, which will be described later. The UV lamp 6 sterilizes the cartridge 3 which is positioned inside the housing 1. For example, a pin type UV lamp 6 can be used so that it can be easily replaced in the lamp socket 113.

The driving unit 7 is a component which is positioned inside the housing 1, and operates the UV lamp 6 and the vaporizer 2. The driving unit 7 includes components such as the pressure sensor 71, a battery 72, a power supply 73, an input 74 and the controller 75.

The pressure sensor 71 is a component which is inserted into the sensor receiving recess 111*a*, and is pressed when the vaporizer receiving portion 41 arrives at the lowermost position, thereby transferring an electrical operation signal to the controller 75. The pressure sensor 71 is connected to the controller 75 via the electric wire 8.

The battery 72 is a component which supplies power for operating the electronic cigarette, and can be implemented as various types of batteries. It is preferred that the battery 72 be implemented as a secondary battery 72 which can be charged to be used, and that the battery 72 be circular shaped.

The power supply 73 is a component which receives external power from a power connector 731.

The input 74 includes a plurality of operation buttons 741 which is disposed on the rear surface of the housing 1, and allows a user to select from among electrical operation signals. When the user pushes a specific operation button, an operation signal corresponding to the specific operation button is output. The operation signals include signals related to the operation of the vaporizer 2 and the operation of the UV lamp 6. For example, when an operation button marked with 1 is pushed, the vaporizer 2 operates, thereby generating smoke.

The controller 75 is a component which controls the electrical operation of the electronic cigarette. The controller 75 charges the battery 72, and operates the UV lamp 6 and the vaporizer 2. The controller 75 includes a vaporizer driving portion 751 which operates the vaporizer 2 following a vaporizer operation signal output from the input 74, a lamp driving portion 752 which operates the UV lamp 6 for a predetermined period following an operation signal output from the pressure sensor 71 or the input 74, a battery charging portion 753 which is supplied with power from the power supply 73 and charges the battery 72, and a controlling portion 754 which controls the overall operation of the controller 75.

Hereinafter, the operating process of the electronic cigarette which includes the above-described configuration will be described with reference to FIG. 1 to FIG. 9. FIG. 7 to FIG. 9 are reference views showing the operating state of the electronic cigarette according to an embodiment of the invention, in which the side plate is removed in order to explain the mechanical operating process inside the electronic cigarette.

A description will be given of the operating principle in which the user breathes in smoke by lifting the cartridge 3. In the state of FIG. 1 and FIG. 7, when the operating lug 42 is moved up, the operating lug 42 pushes down the lower leaf spring 122*a* and moves up along the operating lug movement slit 121. As the operating lug 42 moves up, as shown in FIG. 8, the vaporizer receiving portion 41 also moves up, and consequently, the vaporizer 2 and the cartridge 3 also move up. In addition, as the vaporizer receiving portion 41 moves up, the first rack gear 43 rotates the pinion gear 55 in the clockwise direction, so that the ascending/descending plate 52 moves down. As the ascending/descending plate 52 moves down, the spring 54 is relaxed and the door 51 is opened. Consequently, the ascending/descending plate 52 moves into the housing 1 along the ascending/descending plate guide 16. In the state of FIG. 8, when the operating lug 42 is moved up as far as possible, the door 51 is positioned completely inside the housing 1 and the pressed portion 31 of the cartridge 3 is positioned outside the housing 1 through the opening A, as shown in FIG. 2 and FIG. 9. At this time, the operating lug 42 is supported by the upper leaf spring 122*b*, so that the cartridge 3 is positioned in the state in which it has protruded from the housing 1. In the state in which the pressed portion 31 of the cartridge 3 has protruded from the housing 1, when the user presses one button from among the operating buttons 741, which operates the vaporizer 2, and breathes in by biting the pressed portion 31 by the mouth, the vaporizer 2 operates. Then, the solution that has passed sequentially through the solution containing portion 32, the fiber member 33, the solution collecting portion 221 is heated by the heating coil 222, and is converted into the gaseous state, thereby generating smoke. The smoke flows into the inflow passage under a suction pressure, and enters the mouth of the user through the discharge hole 35.

In sequence, a description will be given of the operating method of moving down and sterilizing the cartridge 3 after the electronic cigarette is used. In the state of FIG. 2 and FIG. 9, when the operating lug 42 is moved down, it operates opposite to the operating process of moving up the cartridge 3. The cartridge 3 moves down through the spate of FIG. 8 and the door 51 closes the opening A, as shown in FIG. 1 and FIG. 7. When the cartridge 3 moves down as far as possible, the lower surface of the vaporizer receiving portion 41 presses the pressure sensor 71, and the pressure sensor 71 transfers a UV lamp operation signal to the controller 75. The controller 75 operates the UV lamp 6 for a predetermined period following the operation signal output from the pressure sensor 71, thereby sterilizing the cartridge 3. Alternatively, the user can press the operating button 741 in order to operate the UV lamp 6, thereby sterilizing the cartridge 3.

The electronic cigarette according to the invention is characterized in that, when the electronic cigarette according to the invention is not being used, the cartridge 3 which is to be held in the mouth is positioned inside the housing 1 and the opening A is closed, thereby preventing the cartridge 3 from being contaminated by impurities such as dust. The electronic cigarette according to the invention is also characterized in that, when the electronic cigarette according to the invention is not being used, the cartridge 3 is positioned inside the housing 1 and is sterilized using the UV lamp 6. Furthermore, the electronic cigarette according to the invention is characterized in that convenience of use is realized and the cartridge 3 is effectively prevented from being contaminated since the opening A is automatically opened and closed following upward and downward movement of the cartridge 3. In addition, the electronic cigarette according to the invention is characterized in that the effect of sterilization can be maximized since the cartridge 3 can be sterilized for a predetermined period as soon as the cartridge 3 is positioned inside the housing 1.

As set forth above, the applicant has explained a variety of embodiments of the invention. However, these embodiments are merely illustrative examples which realize the technical principle of the invention, and any modifications or changes should be interpreted as being embraced in the scope of the invention as long as they embody the technical principle of the invention.

The invention claimed is:

1. An electronic cigarette comprising:
   a housing having an opening;
   an ascending/descending means for moving a cartridge up or down, all or part of the ascending/descending means being positioned inside the housing;
   an opening/closing means which opens or closes the opening by operating in cooperation with the ascending/descending means; and
   an ultraviolet lamp which is positioned inside the housing, and sterilizes the cartridge by irradiating the cartridge with ultraviolet radiation,
   wherein the cartridge contains a solution therein and is moved up or down by the ascending/descending means so that the cartridge is positioned inside the housing or protrudes from the housing through the opening, and the opening can be closed in order to prevent the cartridge from being contaminated by impurities and sterilize the cartridge using the ultraviolet radiation with the cartridge located inside the housing.

2. The electronic cigarette according to claim 1, further comprising a vaporizer which is coupled with one end of the cartridge, is supplied with the solution contained in the cartridge, and generates smoke by vaporizing the solution.

3. The electronic cigarette according to claim 2, wherein
   the housing comprises an operating lug movement slit which is formed in one side surface thereof and extends up and down along the side surface, and
   the ascending/descending means comprises:
   a vaporizer receiving portion which receives therein the vaporizer which is integrally coupled with the cartridge, and is to move up and down; and
   an operating lug which protrudes from one side surface of the vaporizer receiving portion and is inserted into the operating lug movement slit.

4. The electronic cigarette according to claim 1, further comprising a vaporizer which is coupled with one end of the cartridge, is supplied with the solution contained in the cartridge, and generates smoke by vaporizing the solution.

5. The electronic cigarette according to claim 4, wherein
   the housing comprises an operating lug movement slit which is formed in one side surface thereof and extends up and down along the side surface, and
   the ascending/descending means comprises:
   a vaporizer receiving portion which receives therein the vaporizer which is integrally coupled with the cartridge, and is to move up and down; and
   an operating lug which protrudes from one side surface of the vaporizer receiving portion and is inserted into the operating lug movement slit.

6. The electronic cigarette according to claim 5, wherein the opening/closing means includes:
   an ascending/descending plate which is to move up and down;
   a door which is rotatably connected to one end of the ascending/descending plate, and opens or closes the opening following upward or downward movement of the ascending/descending plate; and
   a spring which connects the ascending/descending plate to the door.

7. The electronic cigarette according to claim 6, wherein
   the ascending/descending means further includes a first rack gear which is formed on one side of the vaporizer receiving portion,
   the opening/closing means further includes a pinion gear which meshes with the first rack gear, and
   the ascending/descending plate has a second rack gear which is formed on one side thereof and meshes with the pinion gear.

8. The electronic cigarette according to claim 5, wherein the housing further comprises a leaf spring which is positioned in the operating lug movement slit, and temporarily fixes a position of the operating lug which moves up or down along the operating lug movement slit.

9. The electronic cigarette according to claim 1, further comprising a driving unit which is positioned inside the housing, and operates the ultraviolet lamp and the vaporizer.

10. The electronic cigarette according to claim 9, wherein the driving unit comprises:
    a pressure sensor which is pressed to transfer an electric signal to a controller when the cartridge is positioned inside; and
    the controller which controls an operation of the vaporizer and an operation of the ultraviolet lamp, wherein the controller comprises a lamp driving portion which operates the ultraviolet lamp for a predetermined period following the electric signal generated by the pressure sensor and a vaporizer driving portion which operates the vaporizer.

11. The electronic cigarette according to claim 10, wherein the driving unit further comprises a battery which supplies power to the electronic cigarette, and the controller further comprises a battery charging portion which is supplied with external power and charges the battery.

12. The electronic cigarette according to claim 1, wherein the housing further comprises:
    an upper plate which is detachably coupled with the housing, thereby forming an upper surface of the housing; and
    a cartridge mount which protrudes inside the housing, and receives an extra cartridge therein.

13. An electronic cigarette comprising:
    a housing having an opening:
    an ascending/descending means for moving a cartridge up or down, all or part of the ascending/descending means being positioned inside and housing; and
    the cartridge which contains a solution therein, and is moved up or down by the ascending/descending means so that the cartridge is positioned inside the housing or protrudes from the housing through the opening,
    wherein the cartridge comprises:
    a solution containing portion which is formed at one side of an inner surface of the cartridge, and contains the solution therein;
    an inflow passage through which smoke that is generated while the solution contained in the solution containing portion is passing through the vaporizer is introduced;

a liquid separating portion which removes liquid components contained in the smoke that is introduced through the inflow passage; and a discharge hole through which the smoke, the liquid components of which are removed by the liquid separating portion, is discharged to an outside, wherein the liquid separating portion comprises a lower wing plate which is positioned above the inflow passage, protrudes from one portion of an inner surface of the cartridge, and extends a predetermined length in an opposite direction, and an upper wing plate which is positioned above the lower wing plate, protrudes from the other portion opposite one portion from which the lower wing plate protrudes, and extends a predetermined length in a direction in which the lower wing plate protrudes, whereby, as the smoke that has been introduced through the inflow passage and the liquid components in the smoke comes into contact with the liquid separating portion, a vortex flow is created and a speed of the smoke is decreased, so that the liquid components form droplets on and are trapped by the liquid separating portion; and a trapping member which is connected to a distal end of the upper wing plate, the trapping member having at least one multifaceted member therein.

14. The electronic cigarette according to claim 13, wherein each of the lower wing plate and the upper wing plate has a shape of a wave, and is inclined more downward in a direction toward a distal end thereof.

15. The electronic cigarette according to claim 13, wherein the lower wing plate further comprises a porous member which is positioned at the distal end of the lower wing plate and has a plurality of cavities.

\* \* \* \* \*